(12) United States Patent
Siegel et al.

(10) Patent No.: US 10,458,890 B2
(45) Date of Patent: Oct. 29, 2019

(54) METHOD AND DEVICE FOR DETERMINING THE WEAR PROPERTIES OF COATED FLAT PRODUCTS BY MEANS OF BENDING

(71) Applicant: ThyssenKrupp Steel Europe AG, Duisburg (DE)

(72) Inventors: Marcel Siegel, Duisburg (DE); Peter Heidbuechel, Sonsbeck (DE); Robert Yanik, Moers (DE); Klaus Uran, Moers (DE)

(73) Assignee: ThyssenKrupp Steel Europe AG, Duisburg (DE)

( * ) Notice: Subject to any disclaimer, the term of this patent is extended or adjusted under 35 U.S.C. 154(b) by 0 days.

(21) Appl. No.: 15/105,721

(22) PCT Filed: Dec. 20, 2013

(86) PCT No.: PCT/EP2013/077796
§ 371 (c)(1),
(2) Date: Jun. 17, 2016

(87) PCT Pub. No.: WO2015/090467
PCT Pub. Date: Jun. 25, 2015

(65) Prior Publication Data
US 2017/0023455 A1  Jan. 26, 2017

(51) Int. Cl.
*G01N 3/20* (2006.01)
*G01N 19/04* (2006.01)
(Continued)

(52) U.S. Cl.
CPC ............... *G01N 3/56* (2013.01); *B21D 5/004* (2013.01); *B21D 5/0218* (2013.01); *G01N 3/20* (2013.01); *G01N 19/04* (2013.01)

(58) Field of Classification Search
CPC .............................. G01N 19/04; B21D 5/0254
See application file for complete search history.

(56) References Cited

U.S. PATENT DOCUMENTS 2,339,855 A * 1/1944 Hodil ..................... G01N 19/04
72/213
5,969,973 A * 10/1999 Bourne .................... B21D 5/02
700/165
(Continued)

FOREIGN PATENT DOCUMENTS

CN          1259889 A      7/2000
CN        102712022 A     10/2012
(Continued)

OTHER PUBLICATIONS

Korean IP Office Action for application No. 10-2016-7019475, dated May 8, 2017.*

*Primary Examiner* — Herbert K Roberts
(74) *Attorney, Agent, or Firm* — The Webb Law Firm

(57) ABSTRACT

A method for determining the wear properties of coated flat products such as galvannealed flat steel products is provided herein. In order to be able to achieve better comparability of the determined wear properties of different flat products at least one bending parameter for the bending of the particular flat product by a bending device is selected in accordance with defined criteria on the basis of information regarding the thickness and/or the strength of the particular flat products to be bent. The flat products are bent in the bending device in accordance with the selected bending parameters, wear thus being produced. The wear properties are analyzed in a predetermined manner on the basis of the wear of the particular flat products.

14 Claims, 3 Drawing Sheets

(51) Int. Cl.
  *G01N 3/56* (2006.01)
  *B21D 5/00* (2006.01)
  *B21D 5/02* (2006.01)

(56) References Cited

U.S. PATENT DOCUMENTS

| | | | |
|---|---|---|---|
| 6,266,984 B1 | 7/2001 | Gasparini | |
| 9,339,860 B2 | 5/2016 | Denkmeier | |
| 2010/0147694 A1* | 6/2010 | Nardi | G01N 3/04 |
| | | | 205/81 |
| 2012/0090762 A1* | 4/2012 | Del Sarto | G01N 19/04 |
| | | | 156/64 |

FOREIGN PATENT DOCUMENTS

| | | | |
|---|---|---|---|
| DE | 2844867 A * | 4/1980 | ............... B21D 5/01 |
| DE | 2844867 A1 | 4/1980 | |
| DE | 3914762 A1 | 11/1990 | |
| DE | 4445741 A1 | 6/1996 | |
| JP | 51014133 A | 2/1976 | |
| JP | 57059346 U1 | 4/1982 | |
| JP | 60170529 A | 9/1985 | |
| JP | 6257717 A | 3/1987 | |
| JP | 62100646 A | 5/1987 | |
| JP | 2001353526 A | 12/2001 | |
| JP | 2012115868 A | 6/2012 | |
| KR | 1020070003366 A | 1/2007 | |

\* cited by examiner

METHOD AND DEVICE FOR DETERMINING THE WEAR PROPERTIES OF COATED FLAT PRODUCTS BY MEANS OF BENDING

CROSS-REFERENCE TO RELATED APPLICATION

This application is the United States national phase of International Application No. PCT/EP2013/077796 filed Dec. 20, 2013, the disclosure of which is hereby incorporated in its entirety by reference.

BACKGROUND OF THE INVENTION

Field of the Invention

The invention relates to a method for determining the wear properties of coated flat products, preferably flat metal products, in particular flat steel products. The invention also relates to a bending device for bending coated flat products, preferably flat metal products, in particular flat steel products, to determine the wear properties of the flat products, wherein a bending gap for partially receiving the bent flat product and at least one bending means for bending the flat product at least partially into the bending gap are provided.

Description of Related Art

One property of coated flat products that is very important for many applications is the wear resistance of the coating. Therefore, when manufacturing such flat products particular emphasis is placed on the tendency to wear of the coating. Coated flat products are in particular understood to be metal, steel, light metal or composite flat products, wherein these can, for example, be in the form of strip, sheet, blank or plate. More preferably these products may be hot- or cold-rolled products. Examples of the coating are zinc coatings, which can be provided by hot-dip galvanisation or electrolytic galvanisation of a steel flat product, for example. Such flat products can then be galvannealed. The uncoated flat product can be referred to as a substrate, which supports the coating on at least one side, preferably both sides.

Because of the high demands on the coatings of such flat products, for the purposes of quality control there is considerable interest in the comparative determination of wear properties of various flat products. Steel strips that have been coated by galvannealing, that is, both galvanized and annealed, are by way of example used in the automobile industry, for instance as outer panels, reinforcements or inner parts and must therefore meet high surface requirements. In this connection, a particular problem can be what is known as powdering, which describes a type of wear of the zinc coating during forming processes when particles of the coating break away. This can typically be distinguished from flaking, which involves two-dimensional detachment of the coating.

The tendency of a coated flat product to powdering can be assessed using what is referred to as the adhesive strip bending test. Here, an adhesive strip is affixed to a workpiece sample and this is bent sharply in the area of the adhesive strip, with the result usually being powdering. The adhesive strip can also be affixed to the bent area of the workpiece sample after bending. The particles of the coating that have broken away remain adhered to the adhesive strip, which can if necessary be removed once the workpiece sample has been bent back (flattened) to its initial state. The adhesive strip is then affixed to a white background, such that the particles show up as a grey layer. If the bending has been performed along a bending line, the particles that have broken away are also in a line. The wear properties can be determined by the blackening of the line by the particles of the coating and/or on the basis of the width of the line of particles of the coating. This is also referred to as the degree of powdering.

Determination of the wear properties takes place mainly on a qualitative basis, so that a meaningful assessment of the wear properties of a flat product can only take place by way of a comparison with the wear properties of other flat products. However, this is only possible for flat products coated in the same way and the wear properties of which have been determined in an identical manner. If, for example, the coated flat products differ in terms of thickness and/or strength, lower wear does not necessarily point to better wear properties and vice versa.

The problem for the present invention is therefore to design and develop the abovementioned method and device that have just been described in more detail in such a way as to achieve better comparability of the wear properties of different flat products that have been determined.

SUMMARY OF THE INVENTION

This problem is solved according to the method described herein. Based on information concerning the thickness and/or the strength of the respective flat products to be bent, at least one bending parameter for the bending of the respective flat product with a bending device is selected according to set criteria, wherein the flat products are in each case bent in the bending device according to the selected bending parameter with the creation of wear, and wherein the wear properties of the respective flat products are analysed based on the wear of the respective flat products in a predetermined manner.

The invention has thus identified that comparability of the wear properties of flat products, which differ according to their thickness and/or strength, can be achieved by bending the flat products in different ways. The differences in the bending are specifically predetermined here based, in fact, on the thickness and/or strength of the flat products under investigation. In this way, even with differing flat products, quite reproducible loads during bending can be achieved such that increased wear actually also points to a greater tendency to wear and vice versa. In addition, in the manner described above, the reproducibility of the determination of the wear properties can be improved.

Thus, for certain applications, the wear properties even of essentially different flat products can be compared with a high significance. This means that the wear properties determined in this way can be used not just in connection with quality control, where for a certain test procedure and for a certain flat product a minimum wear property must be demonstrated in order to meet the quality requirements. Rather, the wear properties of differing flat products can be compared with each other. Thus for example the suitability of differing flat products for a particular application can be assessed using the wear properties determined. This can influence whether a particular flat product is used to make a product or if a product is selected for a particular application.

In order to perform the method, information must be known concerning the thickness and/or strength of the flat products to be bent. If necessary, this information is obtained in advance by measurements. Such information can preferably be understood to be (measurement) variables that directly describe the thickness and/or the strength. It also involves information that is dependent upon the size and/or strength of the flat product, however.

Based on this information, prior to the bending process for a particular flat product, at least one bending parameter is then set or selected. The criteria against which this selection takes place are set in advance. Here, the criteria can be determined theoretically and/or empirically. The bending parameters can, by way of example, determine either the way in which the flat product is bent, or the extent of this. The bending parameters can, for example, determine with what and how much the flat product is bent.

In this way, a comparable bending load that can be reproduced from one different flat product to another can be ensured. In addition, if necessary it can be ensured that the bending load does not lead to rupturing of the flat product. On the other hand, however, a bending load that is in the vicinity of the bending load that causes breakage of the flat product can be achieved. The bending load can preferably be at least 75%, in particular at least 85%, preferably 90% of the bending strength. It has proven particularly advantageous if the bending load is at least 95% or between 95% and 99% of the bending load that causes rupturing and/or tensile strength that causes rupturing. This, then, is just below the point at which the workpiece ruptures, something which is to be avoided. It is basically preferred if thicker and/or stronger flat products are bent less, since these fail earlier, and thus even a low amount of bending will already lead to rupture.

In order to ensure the comparability of the amounts of wear created by bending, the wear of each flat product is analysed in a predetermined manner. Here in particular, optical and/or graphical analytical methods are involved. The analysis of the wear results in a characteristic variable that describes the wear properties and/or the amount of wear created during bending. This may involve a grey scale value describing the wear or a measurement of the wear attached to the adhesive strip.

In a first preferred configuration of the method, the bending parameter for the bending of the respective flat product is determined according to set criteria based on information concerning the strength of the respective flat product. In this way, the load acting on the flat product during bending can be set to remain fairly constant for different flat products. With comparable bending loads the extent of the wear is to a large extent determined by the quality of the coating and/or the attachment of the coating to the flat product, thus the substrate of the coated flat product. Basically, a higher tensile strength means a higher resistance to plastic deformation and lower ductility of the material. The bending must therefore take place more cautiously than at lower tensile strengths. The workpiece sample should therefore be bent less far (larger bending angle) and/or with a greater radius (bending radius).

Alternatively or additionally, the comparability of the wear properties determined can be improved if these, based on the wear of the respective flat products, are analysed at least substantially in the same way. Thus, a standardised method can be used, the performance of which is independent of the manner of the previous step of bending and thus of the thickness and/or strength of the flat product. It can be particularly appropriate if wear properties based on the wear of the respective flat products are analysed in an identical manner.

One bending parameter, which can be selected according to the thickness and/or strength of the flat products according to predetermined criteria, is the bending angle, that is, the angle up to which two surfaces of the flat product can be bent together, and/or the bending wedge radius of a bending means used for bending the flat product. The bending wedge radius therefore determines the radius of the bent flat product along the bending line, wherein the bending radius there substantially corresponds to the bending wedge radius. The two bending parameters, thus the bending angle and the bending wedge radius, to a large extent determine the loads for the flat product in the bending process. A bending means in this connection is understood to be a means which during bending pushes against the flat product and thus bends it. In particular, the bending means pushes between two support points for the flat product in the bending device against the flat product. The contact between the flat product and the bending means preferably takes place in the area of the bending gap of the bending device. Here, it is essentially preferred if the bending angle decreases as the thickness increases, as thicker workpiece samples basically only need a low bending angle before they rupture. In addition, it is basically preferred if the bending wedge radius basically increases with the thickness of the flat product, since thick workpiece samples must be bent more cautiously in order to avoid a rupture.

Good results have been achieved with bending angles of between 60° and 120°, in particular between 80° and 110°, more preferably between 90° and 100°. Here, it may be sufficient if a maximum of four, in particular a maximum of three, more preferably a maximum of two, different bending angles are applied. These two bending angles can be 90° and 100°. The bending wedge radii used can for example be between 0.2 and 2.5 mm. Preference here is for the use of a maximum of six, in particular a maximum of four, different bending wedge radii. Here, the bending wedge radii are preferably between 1 mm and 6 mm. Thus, preferably bending wedge radii of 1 mm, 2 mm, 3 mm and/or 6 mm can be used. The stated values of the bending wedge radii and the bending angle allow for example the uniform determination of the wear properties of flat products with a thickness of between 0.5 mm and 3 mm, in particular between 1 mm and 2.5 mm and/or a tensile strength between 250 MPa and 1500 MPa, in particular between 300 MPa and 1200 MPa. For the sake of simplicity, it can be sufficient here, however, if regarding the tensile strength of the workpiece samples to be bent, a distinction is made between a maximum of four tensile strength intervals, in order to select the at least one bending parameter. For the same reason, more preferably for selection of the at least one bending parameter a distinction may be made between just two tensile strength intervals. The tensile strength intervals can for example comprise on the one hand tensile strengths of up to 700 MPa and on the other tensile strengths of more than 700 MPa up to and including 1,200 MPa.

For the adjustment or selection of the bending wedge radius it is a good idea if prior to bending the flat products in each case as a function of the bending wedge radius selected a corresponding bending means, in particular an appropriate bending wedge, is selected. Here, the flat products are bent with the bending means selected in each case. Thus, there is no need for a cumbersome modification of the bending wedge radius of a single bending means prior to the bending process. Rather, for the sake of simplicity, the bending means is selected from a plurality of bending means with differing bending wedge radii which according to the predetermined criteria has the desired bending wedge radius for bending a particular flat product.

In order to ensure that the predetermined bending angle can also be achieved fairly precisely during the bending process, prior to bending the flat products in each case, as a function of the bending angle selected, the plunging depth of the bending means can be selected. The plunging depth of the bending means, preferably of the bending wedge, into the bending gap determines the bending angle to be achieved at least to a large extent.

In this connection, for the sake of simplicity the distance traveled by the bending means during the bending process from contact with the as yet unbent flat product until the final position in the bending gap can be taken as the plunging depth. The plunging depth thus determines how far the bending means plunges into the bending gap. Here, advantage can be taken of the fact that the plunging depth can be set and adjusted very easily and precisely.

In order that the bending process can be defined based on the information concerning the thickness and/or the strength of the flat product to be bent, it is a good idea if this information is transmitted to the bending device, in particular to a control device. Alternatively, of course, it can be provided that this information is determined in the bending device and/or an associated measuring device for each flat product prior to the bending process, although this can be more complicated in terms of the design and the method.

In order to be able to determine the wear properties in a reproducible manner based on the wear caused during bending, it is a good idea if prior to, during or after the bending in each case an adhesive means, preferably an adhesive strip, is affixed to the respective flat product to receive at least part of the wear. If the adhesive means is applied after bending, wear may already have been lost during bending and not taken into account in the subsequent analysis of the wear. While affixing of the adhesive strip during bending is actually possible, because of the high level of effort it is rather less preferred. The adhesive means is in any case removed after bending, in particular after bending back or flattening of the flat product, from the flat product. In doing so the intention is that as much as possible of the wear in each case remains on the respective adhesive means, in order to be able to carry out a meaningful analysis of the wear for determining the wear properties of the flat products. It is therefore also a good idea if the flat products after bending are at least partially bent back or returned to the flat starting shape (flattening). In the flattened state the wear released from the coating will come away more easily. This avoids particles of the coating that have actually come loose not being able to be removed with the adhesive means as a result of pinching. To flatten it the bent flat product can be placed on a flat support and by means of a similarly flat stamp pushed down (flat).

The abovementioned object is also achieved by a device according to the preamble of claim 10 in that a control device is provided for controlling at least one bending parameter during bending of the at least one flat product, and in that the control device is provided for changing the at least one bending parameter according to predetermined criteria based on information concerning the thickness and/or the strength between at least two bending processes.

The control device controls at least one bending parameter as a function of the thickness and/or the strength of the flat product to be bent. The bending parameter is thus varied between two bending processes with the help of the control device, if on the bending devices flat products with sufficiently different thicknesses and/or strengths are being bent. How the bending parameter is to be varied as a function of the thickness and/or the strength of the flat product by the control device, is determined on the basis of the previously set criteria.

In a corresponding way, a comparable loading during bending of different flat products is achieved. Thus, the extent of the wear achieved during bending is also comparable. If now in a comparable manner the wear properties are determined on the basis of the respective wear, the wear properties of different flat products are to a large extent comparable. Ultimately the advantages already described in connection with the method are achieved. The descriptions of the method are in any case basically transferrable to the descriptions of the device and vice versa.

In a first preferred configuration of the bending device a plurality of bending means, preferably in the form of bending wedges, is provided. From these bending means according to predetermined criteria based on the information concerning the thickness and/or the strength of the flat product a suitable bending means, for example with a suitable bending wedge radius, can be selected and used for bending. To simplify this a bending means exchange device can be provided which between at least two bending processes according to the instructions of the control device changes the bending means used for bending in each case, in particular automatically, so that the user of the bending device does not have to manually intervene.

The bending means exchange device can comprise a turret head supporting a plurality of bending means. With the help of the turret head between at least two bending processes the bending means used for bending in each case can be changed. The configuration in the form of a turret head allows simple changing of the bending means merely by rotation of the turret head into the desired position, in which the desired bending means is active, that is to say can be used for bending.

In order in each case to bend the flat products fairly precisely at a certain bending angle around the bending means, the bending means used in each case for bending and/or the bending gap can be associated with a moving device, which ensures the plunging of the at least one bending means to a maximum plunging depth specified by the control device. Here the bending gap is preferably moved relative to the bending means and/or the bending means relative to the bending gap. The control device also specifies the plunging depth, and in particular based on the thickness and/or the strength of the flat products to be bent and according to specified criteria. Therefore, the maximum plunging depth of the bending means into the bending gap can be changed specifically between two consecutive bending processes.

It is also appropriate for the control device to have at least one interface for receiving and one processing unit for processing the information concerning the thickness and/or the strength of the flat products to be bent. Then, together with the flat product to be bent, the bending device can also be provided with information concerning the thickness and/or the strength of the flat product, allowing the control device, in particular the processing unit, to select at least one bending parameter according to certain instructions for bending the corresponding flat product.

Here, the control device is preferably designed to change the at least one bending parameter according to predetermined criteria, based on information concerning the tensile strength, between at least two successive bending processes.

EXAMPLE

The criteria according to which the control device can specify the bending wedge radius and the bending angle for bending a particular flat product based on the information concerning the thickness and the tensile strength of the flat product, are shown by way of example in the table below:

| Tensile strength of the flat product <700 MPa | | | |
|---|---|---|---|
| Thickness | 0.5-1.1 mm | 1.2-2 mm | 2.1-2.6 mm |
| Bending wedge radius | 1 mm | 1 mm | 2 mm |
| Bending angle | 90° | 100° | 100° |
| Tensile strength of the flat product 700 MPa-1000 MPa | | | |
| Thickness | 0.7-1.1 mm | 1.2-1.4 mm | 1.5-1.8 mm |
| Bending wedge radius | 1 mm | 3 mm | 3 mm |
| Bending angle | 100° | 90° | 100° |
| Thickness | 1.9-2.2 mm | 2.3-2.5 mm | |
| Bending wedge radius | 6 mm | 6 mm | |
| Bending angle | 90° | 100° | |

BRIEF DESCRIPTION OF THE DRAWINGS

In the following, the invention is explained in more detail using a drawing showing a single embodiment.

The drawing shows as follows.

DESCRIPTION OF THE INVENTION

Figure 1:
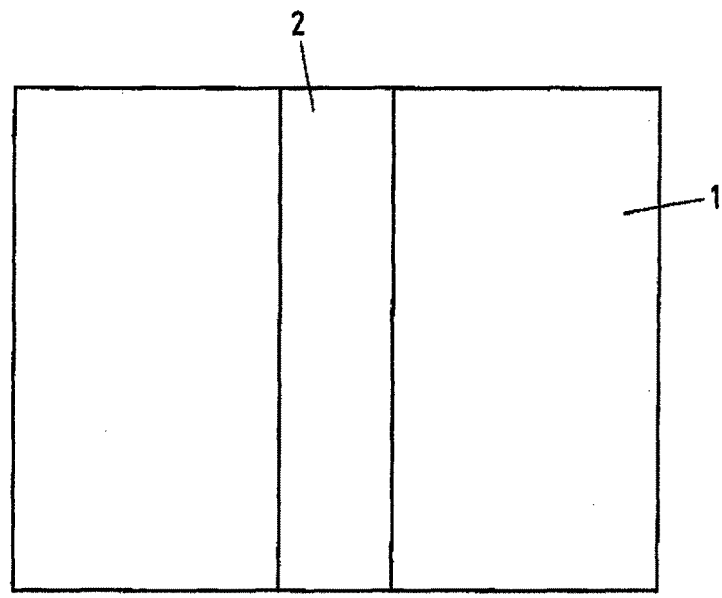
FIG. 1 a top view of a coated flat product provided with an adhesive strip.
Figure 2:
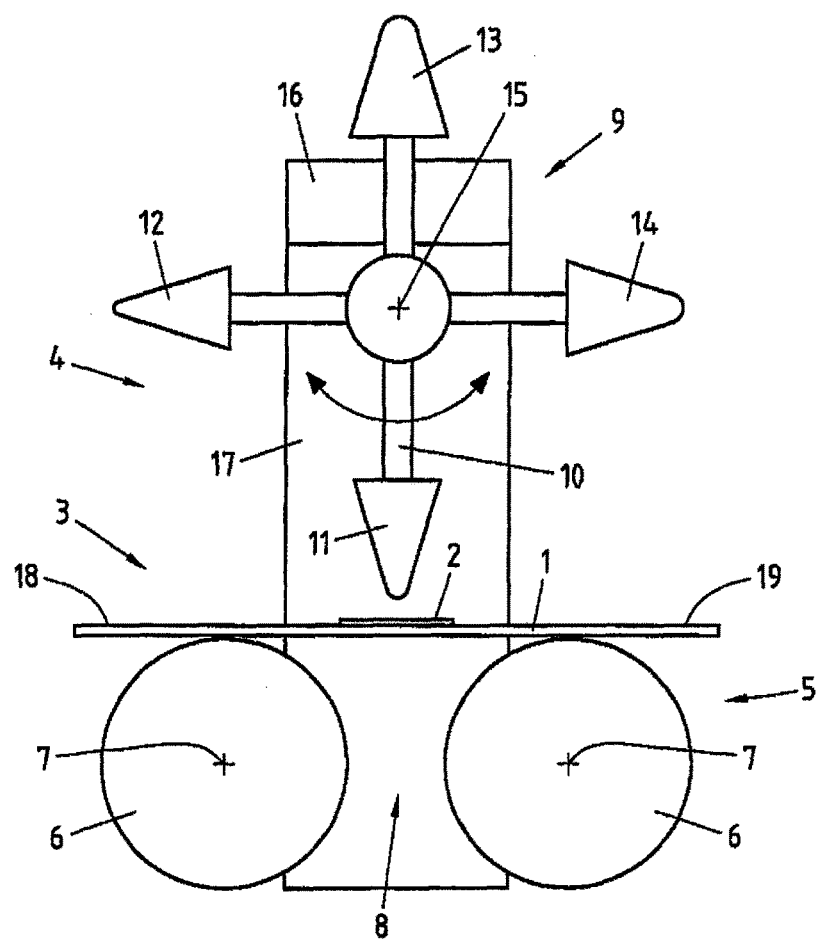
FIG. 2 a side view of a bending device according to the invention with the flat product from FIG. 1 in the as yet unbent state.

FIG. 1 shows a top view of a coated flat product 1 in the form of a galvannealed coated steel strip, the wear properties of which are to be investigated. To this end, an adhesive means in the form of an adhesive strip 2, preferably in plastic, in particular a transparent plastic, is affixed to the flat product 1. The flat product 1 provided with the adhesive strip 2 is placed in a seat 3 of the bending device 4, shown in FIG. 2. There the flat product 1 is placed in a starting position on what is known as a roller die 5. Instead of a roller die 5 with two rollers 6, rotatable about two parallel axes 7, each aligned parallel to the plane of the unbent flat product 1, another die, referred to as a V-die, could be provided, having a V-shaped slot for making a bend in the flat product 1. A die could also be used having two supports arranged parallel to one another, and which are rounded where they are adjacent to the bending gap, or a die with fixed, that is to say non-rotatable, rollers. The roller die 5 shown, and to this extent preferred, comprises two rollers 6, each with a diameter of 50 mm. Basically, however, other roller diameters can also be used. The rollers 6 form a bending gap 8 between them with a minimum width at the narrowest point of the bending gap 8 of 6 mm parallel to the plane of the flat product 1 in the unbent initial state according to FIG. 2. The bending gap could basically also be variable. To this end, a spring mounting of at least one roller could be provided such that the bending gap becomes wider the higher the force is exerted in the roller, in particular the at least one corresponding spring. It can also be provided that the bending gap widens if the force exerted on at the at least one spring-mounted roller exceeds a certain amount.

Above the unbent flat product 1 a bending means exchange device 9 in the form of a turret head 10 with four bending wedges 11, 12, 13, 14 is provided, which is similarly rotatable about an axis 15 parallel to the plane of the unbent flat product 1, in order in this way to be able to bend the flat product 1 with the desired bending wedge 11, 12, 13, 14. To this end, the turret head 10 simply has to be rotated into a corresponding position. The position, into which the turret head 10 is rotated, is specified by a control device 16. The control device 16 is transmitted information via an interface (not shown) concerning the thickness and the strength, in particular the tensile strength, of the flat product 1 to be bent, which is processed by a processing unit (also not shown). Based on this information the control device 16 controls the turret head 10, so that this rotates in such a way that the flat product 1 is bent with the bending wedge 11 with the desired bending wedge radius. The criteria against which the bending wedge radius is selected, have been set in advance. The criteria are preferably stored in the memory unit. For a particular combination of thickness and strength of the flat product 1 it is preferably empirically determined in advance, which bending wedge radius and bending angle α are to be used to cause a bending of the flat product 1, which is comparable with the bending of flat products 1 of other thicknesses and strengths in terms of the creation of wear.

Figure 3:
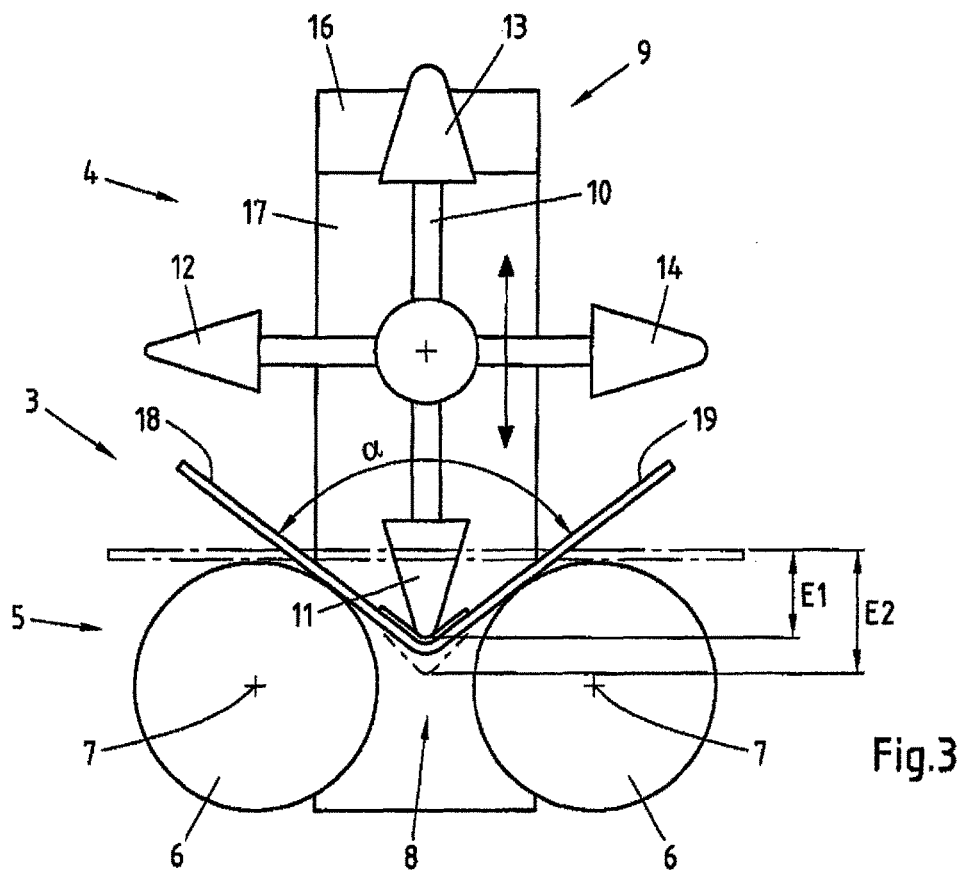
FIG. 3 a side view of the bending device from FIG. 2 with the flat product from FIG. 2 in the bent state.

The turret head 10 with the four bending wedges 11, 12, 13, 14 is secured to a moving device 17. The moving device 17 is designed so that the bending wedge 11 pointing in the direction of the flat product 1 can be moved into the bending gap 8. The extent to which the bending wedge 11 is moved into the bending gap 8, is controlled by the control device 16. Here, the control device 16, based on the information concerning the thickness and strength of the flat product 1 to be bent, determines how far the bending wedge 11 is moved into the bending gap 8. Here, the further the bending wedge 11 is moved into the bending gap 8, the smaller the bending angle α, that is the angle between the faces 18, 19 of the flat product being bent together, becomes. Here, the bending angle α for a given die is essentially directly correlated with what is referred to as the plunging depth of the bending wedge. The plunging depth is shown in FIG. 3. The plunging depth E1 corresponds here to a bending angle α of approximately 100°, while the plunging depth E2 corresponds to a bending angle α of approximately 90°. The plunging depth is given here by the distance between the surface of the unbent flat product 1 and the underside of the bending wedge 11, 12, 13, 14 in the position of maximum insertion of the bending wedge 11, 12, 13, 14 during the respective bending process.

Figure 4:
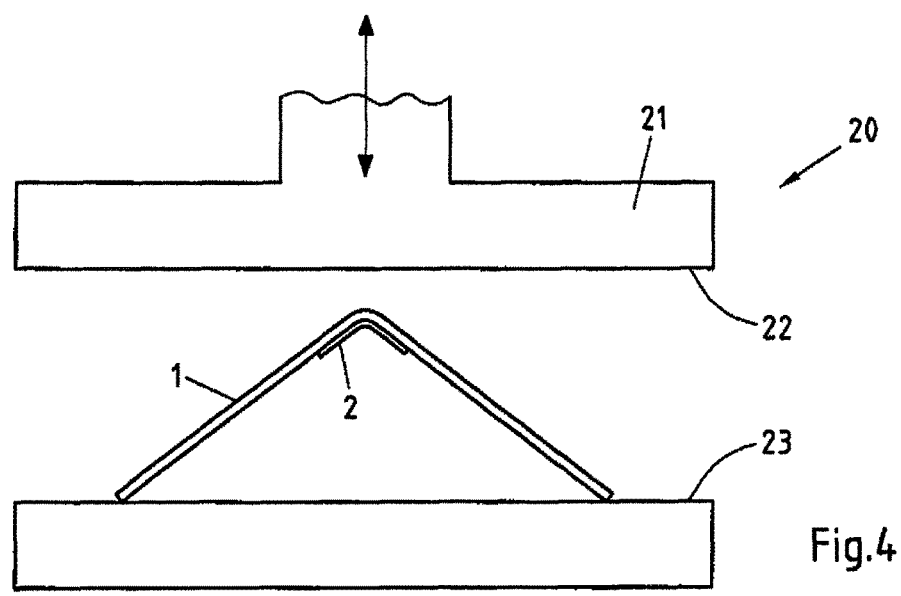
FIG. 4 a side view of a flattening device with the flat product from FIG. 3.
Figure 5:
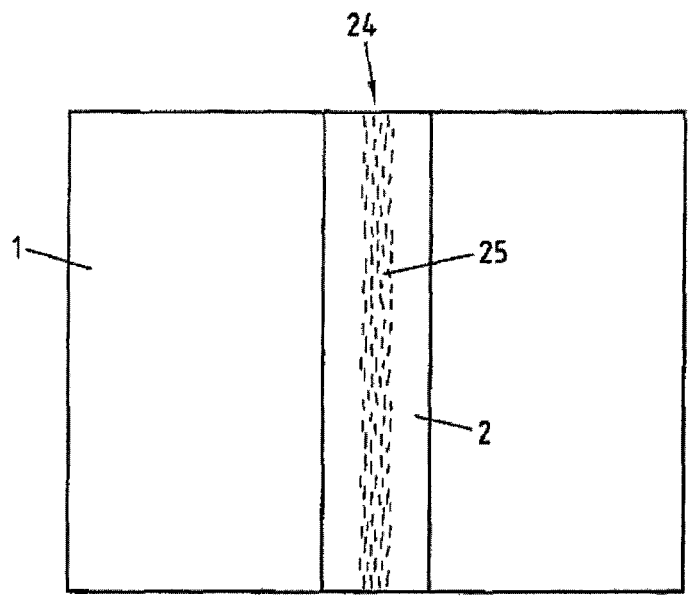
FIG. 5 a top view of the flat product from FIG. 3 provided with the adhesive strip after flattening.

After bending, the bent flat product 1 is removed from the bending device 4 and flattened in a flattening device 20 according to FIG. 4 between a stamp 21 with a flat underside 22 and a flat support 23. Here, the bending of the flat product 1 is reversed and the flat product 1 reverted to a flat form. In this way, the flat product 1 according to FIG. 5 is obtained. The flat product 1 was bent about a bending line 24 along the adhesive strip 2, leading to wear 25 there, present as a strip lengthways to the adhesive strip 2 and adhering to the adhesive strip 2. The wear 25 can thus be removed with the adhesive strip 2 from the flat product 1 and then analysed, to indicate the wear properties. The wear properties can thus be expressed as the degree of blackening, or what is known as the grey scale of the strip of wear 25. Alternatively, however, the width of the strip of wear 25 can be determined and used to express the wear properties. It is essentially the case that the more wear 25 created during bending, the wider and blacker the strip is. The way in which the adhesive strip 2 together with the wear 25 is assessed and the determination of the wear properties can be carried out as described in the state of the art regarding what is known as the adhesive strip bending test or also the V bending test.

Figure 6:
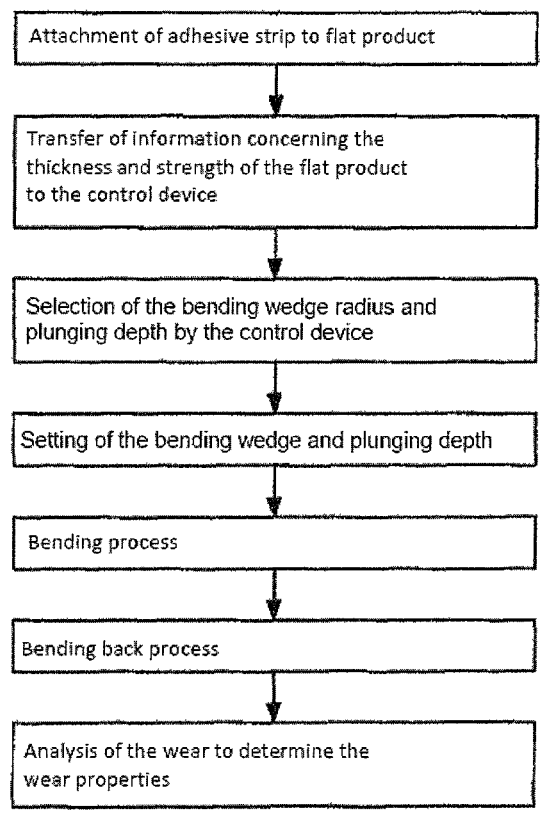
FIG. 6 a schematic flow diagram of a method according to the invention.

FIG. 6 is a schematic representation of the sequence of a method of the abovementioned kind. Initially an adhesive strip is attached to a coated flat product, preferably in the form of a galvannealed coated steel sheet, according to the method described and to this extent preferred method. The flat product is preferably then placed in a seat of a bending device on a die. In addition, the thickness and the strength of the flat product are passed on to the control device of a bending device. Based on the information concerning the thickness and the strength of the flat product a bending wedge radius and a plunging depth are selected and set for the bending process. The flat product is then bent with the help of the bending wedge, which together with the flat product plunges by a predetermined distance into the bending gap. Then the flat product is removed from the bending device and is pressed flat again or bent back in a flattening device. Alternatively, though, the flattening device can be incorporated into the bending device. This is in particular possible if the turret head 10 in addition to the bending wedges also has a flattening stamp with a flattening surface, which to flatten the bent flat product can be rotated into position, in order to interact with the die for flattening the flat product. Then the adhesive strip together with the wear created during bending is preferably removed from the flat product and, based on the adhesive strip, the wear properties of the corresponding flat product are determined.

The method steps described above for a flat product are performed in succession for different flat products, which differ in terms of their thickness and/or strength. The correspondingly determined wear properties, despite these differences, are to a large extent comparable with one another.

The invention claimed is:

1. A method for determining wear properties of coated flat products comprising:
   determining a thickness and a strength of a coated flat product,
   selecting at least one bending parameter for bending the coated flat product with a bending device according to set criteria, wherein the set criteria is based on information concerning at least one of the thickness and the strength of the coated flat product to be bent,
   bending the coated flat product in the bending device according to the at least one selected bending parameter, thereby creating wear of the coated flat product, and
   analysing the wear properties based on the wear of the coated flat product in a predetermined manner,
   wherein the set criteria is a bending load applied to the coated flat product that is a predetermined percentage of a bending strength of the coated flat product such that wear properties of the coating of the coated flat product are determined exclusive of any effect of the thickness and the strength of the coated flat product,
   wherein the bending load is 75-99% of the bending strength of the coated flat product,
   wherein an adhesive is affixed to the coated flat product, prior to the bending of the coated flat product, to receive at least part of the wear of the coated flat product, wherein the adhesive, together with part of the wear adhering to the adhesive, is removed from the coated flat product and analysed to determine the wear properties of the coated flat product, and
   wherein the bending device comprises a rotatable turret head supporting a plurality of bending tools and a respective one of the plurality of bending tools used for the bending can be changed between at least two bending processes by rotation of the turret head.

2. The method according to claim 1, wherein the at least one bending parameter for the bending of the coated flat product is selected according to set criteria based on information concerning a tensile strength of the coated flat product.

3. The method according to claim 1, wherein the determining, the selecting, the bending, and the analysing are performed on a plurality of coated flat products and the wear properties of each of the plurality of coated flat products are analysed substantially in the same way.

4. The method according to claim 1, wherein the at least one bending parameter is at least one of a bending angle and a bending wedge radius for bending the coated flat product in the bending device.

5. The method according to claim 4, wherein the respective bending tool is selected as a function of the bending wedge radius.

6. The method according to claim 5, wherein a plunging depth of the respective bending tool in a bending gap is selected in each case as a function of the bending angle prior to bending the coated flat product.

7. The method according to claim 6, wherein the plunging depth is a distance traveled by the respective bending tool during the bending process from initial contact with the coated flat product until a final position in the bending gap.

8. The method according to claim 1, wherein the bending device is transmitted information concerning at least one of the thickness and the strength of the coated flat product to be bent.

9. The method according to claim 1, wherein the bending device comprises:
   a bending gap for partially receiving the bent coated flat product and the respective bending tool into the bending gap, and
   a control device for controlling the at least one bending parameter during bending of the coated flat product,
   wherein the control device is configured to change the at least one bending parameter according to the set criteria between at least two bending processes, and
   wherein the control device selects the at least one bending parameter to apply the bending load.

10. The method according to claim 9, wherein at least one of the respective bending tool used for bending and the bending gap is associated with a moving device, which plunges the respective bending tool up to a maximum plunging depth specified by the control device into the bending gap, and wherein the maximum plunging depth of the respective bending tool created by the moving device can be changed between the at least two bending processes by the control device according to certain instructions.

11. The method according to claim 9, wherein the control device has at least one interface for receiving and one processing unit for processing the information concerning at least one of the thickness and the strength of the coated flat product to be bent.

12. The method according to claim 9, wherein the control device is provided to change the at least one bending parameter according to predetermined criteria, based on information concerning a tensile strength, between the at least two bending processes.

13. The method according to claim 1, wherein the adhesive comprises an adhesive strip.

14. The method according to claim 9, wherein the plurality of bending tools comprises bending wedges.

* * * * *